United States Patent
McHugo

(10) Patent No.: US 9,980,833 B2
(45) Date of Patent: May 29, 2018

(54) UNIFORM EXPANDABLE AND COLLAPSIBLE STENT

(75) Inventor: Vincent McHugo, Co. Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days. days.

(21) Appl. No.: 13/564,134

(22) Filed: Aug. 1, 2012

(65) Prior Publication Data

US 2013/0173017 A1    Jul. 4, 2013

Related U.S. Application Data

(60) Provisional application No. 61/515,208, filed on Aug. 4, 2011.

(51) Int. Cl.
*A61F 2/88* (2006.01)
*A61F 2/852* (2013.01)
*A61F 2/90* (2013.01)

(52) U.S. Cl.
CPC .............. *A61F 2/88* (2013.01); *A61F 2/852* (2013.01); *A61F 2/885* (2013.01); *A61F 2/90* (2013.01)

(58) Field of Classification Search
CPC ...... A61F 2/04; A61F 2/06; A61F 2/82; A61F 2/88; A61F 2/852; A61F 2/885
USPC ................................................. 623/1.22, 23.69
See application file for complete search history.

(56) References Cited

U.S. PATENT DOCUMENTS

| | | | |
|---|---|---|---|
| 7,211,109 B2 * | 5/2007 | Thompson | 623/1.53 |
| 2007/0038290 A1 * | 2/2007 | Huang et al. | 623/1.16 |
| 2011/0087146 A1 * | 4/2011 | Ryan et al. | 604/8 |
| 2011/0144739 A1 * | 6/2011 | Cattaneo | 623/1.22 |

FOREIGN PATENT DOCUMENTS

WO    WO 99/30639    *    6/1999    .............. A61F 2/06

* cited by examiner

*Primary Examiner* — Dinah Baria
(74) *Attorney, Agent, or Firm* — Brinks Gilson & Lione

(57) ABSTRACT

A modified double helical and braided (platted) helical wire stent is described that provides for uniform collapsing and expansion of the stent body such that the stent collapses and expands in a uniform, predictable manner, reduces foreshortening, and is durable, stable, and reliable.

10 Claims, 6 Drawing Sheets

UNIFORM EXPANDABLE AND COLLAPSIBLE STENT

RELATED APPLICATION

This application claims the benefit of priority from U.S. Provisional Application No. 61/515,208, filed Aug. 4, 2011, and titled "Uniform Expandable And Collapsible Stent", the contents of which is incorporated herein by reference.

TECHNICAL FIELD

The present invention relates to indwelling medical devices and more specifically, stents.

BACKGROUND

Self-expanding stents are useful for a variety of procedures requiring the maintenance of the patency of a bodily pathway. Such stents are generally biased to expand, such that when deployed, they assume an open position, pushing outward and into the surrounding area into which deployed. The radial expansion creates or maintains a pathway in a once occluded or weak area.

Avoiding the use of a sheath for deploying a stent, such as a self-expanding stent, is desired to avoid many of the shortcomings resulting from sheath deployment. For example, the sheath release delivery devices are difficult to reposition or remove and slow to operate. The stent may only be partially deployed prior to reconstrainment of the stent by the sheath in order to still reposition or remove the stent. Once the stent is fully deployed, i.e. radially expanded, the sheath cannot reconstrain the stent to allow it to be repositioned or removed. For example, utilizing a conventional outer sheath/inner catheter delivery device may cause the physician to inadvertently use excessive force and pull back the outer sheath too far, thereby prematurely deploying the stent in an incorrect position within a bodily lumen. At this step in the procedure, repositioning of the stent becomes difficult, if not impossible, because the stent has already radially self-expanded into the bodily lumen. Additionally, retraction of the outer sheath in a controlled manner is often difficult which may lead to uneven or inadvertent jerking back of the outer sheath and improper positioning of the stent.

Moreover, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the proximal portion of the stent may elongate or foreshorten while still covered by the outer sheath or after the sheath releases the stent. Thus, the positioning of the stent body in the central portion of the target region may be difficult with a distal stent release system. An additional drawback occurs with the sheathed stent delivery system where direct visualization of the stent is required. For example, in endoscopically placed stents, the sheath tends to prevent or obscure the location of the stent, making accurate placement of the stent more difficult. Accurate placement of the proximal portion of the stent and/or the stent body may be important in certain applications, for example to prevent stent migration or to properly open a stricture along the entire length of the stricture.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catheters and hysterics in the movement of the stent. The sheathed stent delivery device also requires more space within an endoscope compared to a sheathless device and also adds additional expense to the delivery system.

Double-helical self-expanding wire stents that are able to assume a compressed state (i.e., a state wherein the diameter of the stent is less than when the stent is expanded) without the use of a sheath have been developed. For example, referring to FIGS. 1A-1C, self-expanding stents have been developed that may be constrained by rotating the ends of the stent in opposite directions. However, these stents may not compress or deploy in a uniform, predictable manner. Thus, while avoiding the shortcomings from using a sheath, these types of stents may present different drawbacks. For example, when in a compressed, un-expanded state, the stent's outer surface is not uniform throughout, and generally, a ridge on the outer surface of the stent is created during compression. When expanding, such stents may pop open and radially expand in a jumpy, non-uniform manner. The stent's non-uniform compression and expansion make deployment and repositioning the stent difficult due to the unpredictability of the stent's physical behavior.

BRIEF SUMMARY

In a first aspect, a stent is provided including a wire configured into an elongated tubular helical pattern including a proximal portion, a distal portion, a lumen extending between the proximal portion and the distal portion, and a first diameter of the elongated tubular helical pattern, wherein the elongated tubular helical pattern is configurable into a radially compressed state comprising a second diameter less than the first diameter when a rotational force is applied to the proximal portion of the elongated tubular helical pattern and an opposite rotational force is applied to the distal portion of the elongated tubular helical pattern; wherein when in the radially compressed state, the elongated tubular helical pattern is biased to assume an uncompressed state; and a suture configured into an elongated tubular helical pattern comprising a pitch about opposite the elongated tubular helical pattern of the wire, wherein the elongated tubular helical pattern of the suture comprises a proximal portion and a distal portion; wherein the elongated tubular helical pattern of the wire and the elongated tubular helical pattern of the suture are in communication with each other to form a stent wall comprising a double helical pattern.

In a second aspect, a method of deploying a stent is provided, the method including providing a stent comprising a proximal portion, distal portion, a lumen extending between the proximal portion and the distal portion; and a wall comprising a mesh configuration; providing an introducer comprising a proximal portion and a distal portion; loading the stent onto the introducer such that the proximal portion of the stent is attached to the proximal portion of the introducer and the distal portion of the stent is attached to the distal portion of the introducer; rotating the proximal portion of the introducer in a first direction and the distal portion of the introducer in a second direction about opposite to the first direction causing the stent to collapse evenly without forming a ridge.

In a third aspect, a method for manufacturing a stent is provided, the method including forming a first elongated tubular body including a wire wrapped in a first helical orientation; and forming a second elongated tubular body including a suture wrapped in a second helical orientation including a pitch about opposite the first helical orientation, wherein the first elongated tubular body and the second elongated tubular body are in communication with each other and are coaxial forming a stent wall comprising a double helical pattern.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims.

DETAILED DESCRIPTION OF PRESENTLY PREFERRED EMBODIMENTS

The exemplary embodiments illustrated herein provide exemplary apparatuses for uniform, predictable constrainment and radial expansion of a self-expanding stent using the torsion of its body such that it is collapses in about an even, uniform manner thereby reducing non-uniform expansion and unpredictable stent jumping upon expansion. The present discovery is not limited to those embodiments described herein, but rather, the disclosure includes all equivalents and those intended to be included in the claims. For example, the principles herein can be applied to other types of stents, including but not limited to, self-expanding metal stents, self-expanding laser cut peripheral artery stents, laser cut self-expanding stents, woven wire stents, and the EVOLUTION® (Wilson-Cook Medical Inc.).

Moreover, the embodiments illustrated herein can be used in any portion of the body benefiting from an indwelling medical device, such as a stent, that collapses and expands in a uniform, predictable manner without the use of a introducer sheath, thereby permitting the stent to be easily deployed, removed, and repositioned including but not limited to, the gastrointestinal region, esophageal region, duodenum region, biliary region, colonic region, as well as any other bodily region or field, and they are not limited to the sizes, shapes, or configurations illustrated herein.

The term patient, as used herein, is not limited to being a human being, indeed animals and others are contemplated. User, as used herein, is anyone or thing capable of using the device, including but not limited to, a human being and machine.

Figure 1A:
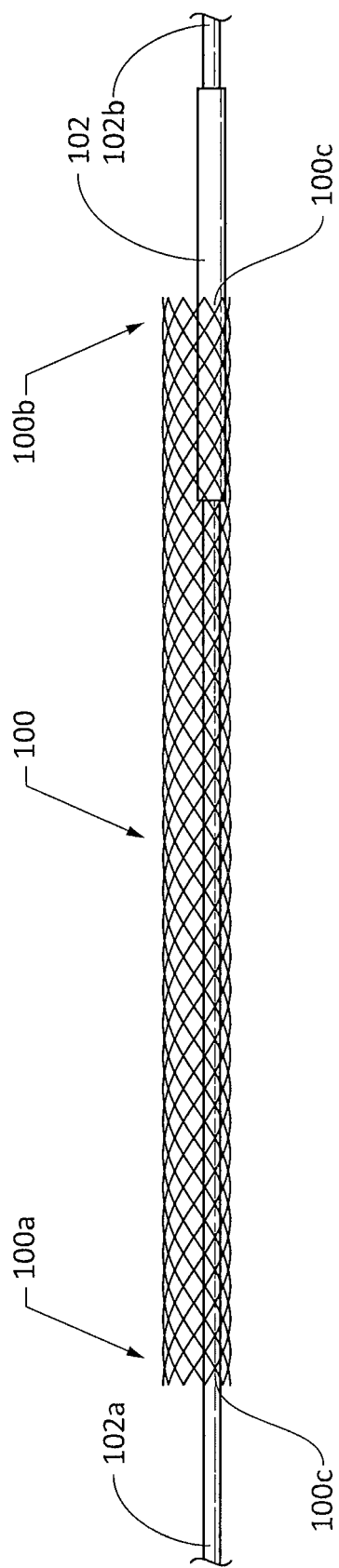
FIG. 1A illustrates a side view of a double helical stent in an expanded state mounted onto an exemplary torsion constrainment introducer.

As discussed above referring to FIGS. 1A-1C, self-expanding stent have been developed that may be constrained by rotating the ends of the stent in opposite directions. FIG. 1A illustrates a side view of double helical stent 100 in an expanded state mounted onto exemplary torsion constrainment introducer 102. Stent 100 has proximal portion 100a, distal portion 100b, and lumen 100c extending throughout. Stent 100 is a double helical wire stent made from one or more woven nickel titanium (nitinol) wires that are heat-set such that the wires are biased to assume an expanded state, as illustrated in FIG. 1A.

Figure 1B:
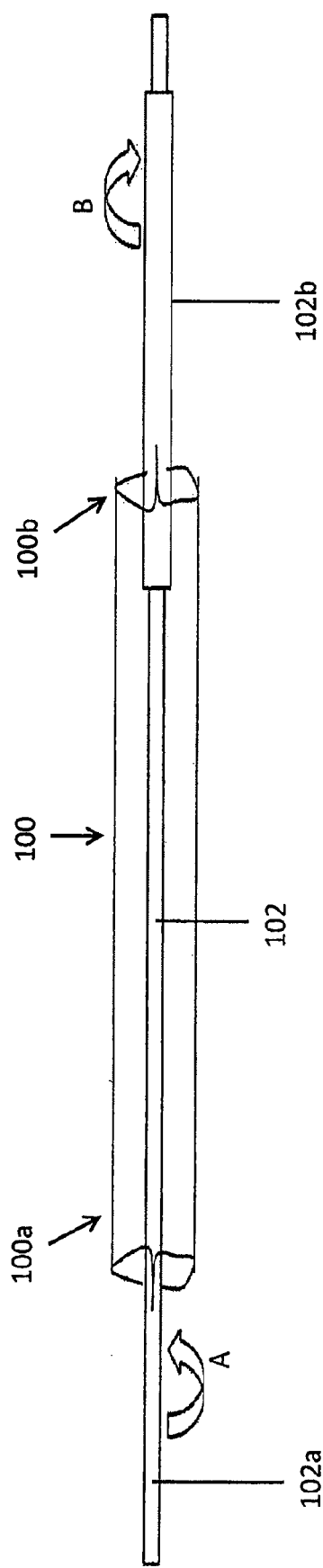
FIG. 1B illustrates a cross-sectional view of a double helical stent mounted onto an exemplary torsion constrainment introducer being compressed.

Referring to FIGS. 1A and 1B, stent 100 is shown mounted onto exemplary torsion constrainment introducer delivery system 102, such as that described in U.S. Provisional Patent Appl. Ser. No. 61/407,635, entitled "Torsion Constrained Stent Delivery System," filed Oct. 28, 2010, and incorporated in its entirety herein by reference. Proximal portion 100a of stent 100 is attached to proximal portion of introducer 102a, and distal portion 100b of stent 100 is attached to distal portion of introducer 102b.

FIG. 1B illustrates a cross-sectional view of double helical stent 100 mounted onto exemplary torsion constrainment introducer 102 wherein stent 100 is being compressed. Proximal portion 102a and distal portion 102b of torsion constrainment introducer 102 are being rotated in opposite directions as illustrated by Arrows A and B. The opposite rotational force applied via introducer (or any other means) causes stent 100 to collapse into a compressed state onto introducer 102.

Figure 1C:
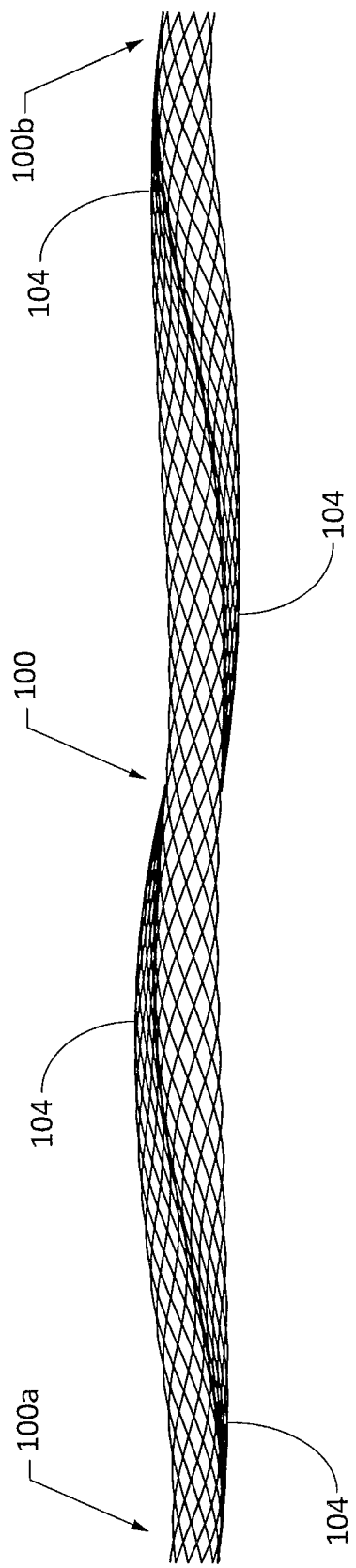
FIG. 1C illustrates a side view of a double helical stent in a compressed state.

FIG. 1C illustrates a side view of double helical stent 100 in a compressed state. Stent 100, is compressed, collapsed, having opposite rotational forces applied to proximal portion 100a and distal portion 100b, such as that illustrated in FIG. 1B. Referring again to FIG. 1C, stent 100, when in a collapsed, compressed state, forms ridge 104 that runs along stent 100 thereby reducing the uniform outer surface of stent.

As illustrated in FIG. 1C, stent 100 has not evenly collapsed as evinced by ridge 104. Ridge 104 increases the diameter of stent 100 in the collapsed state. Ridge 104 also stores energy that causes the opening, expansion of stent, such as when it is deployed, to be in a jumpy and unpredictable manner. Thus, proximal portion 100a of stent 100 may expand at a rate different from the rest of stent 100, and distal portion 100b of stent 100 may expand at a rate different from the rest of stent 100.

A more detailed description of the embodiments will now be given with reference to FIGS. 2-4. Throughout the disclosure, like reference numerals and letters refer to like elements. The present disclosure is not limited to the embodiments illustrated; to the contrary, the present disclosure specifically contemplates other embodiments not illustrated but intended to be included in the claims.

It has been discovered that modifying a sent can overcome the limitations of a typical double helical stent, such as that illustrated in FIGS. 1A-1C, including but not limited to, the stent collapsing and expanding in a non-uniform, unpredictable manner, thus providing a stent that collapses and expands in a uniform, predictable manner that is durable, stable, and reliable, thereby making stent placement, deployment, removal, and repositioning easier.

Figure 2:
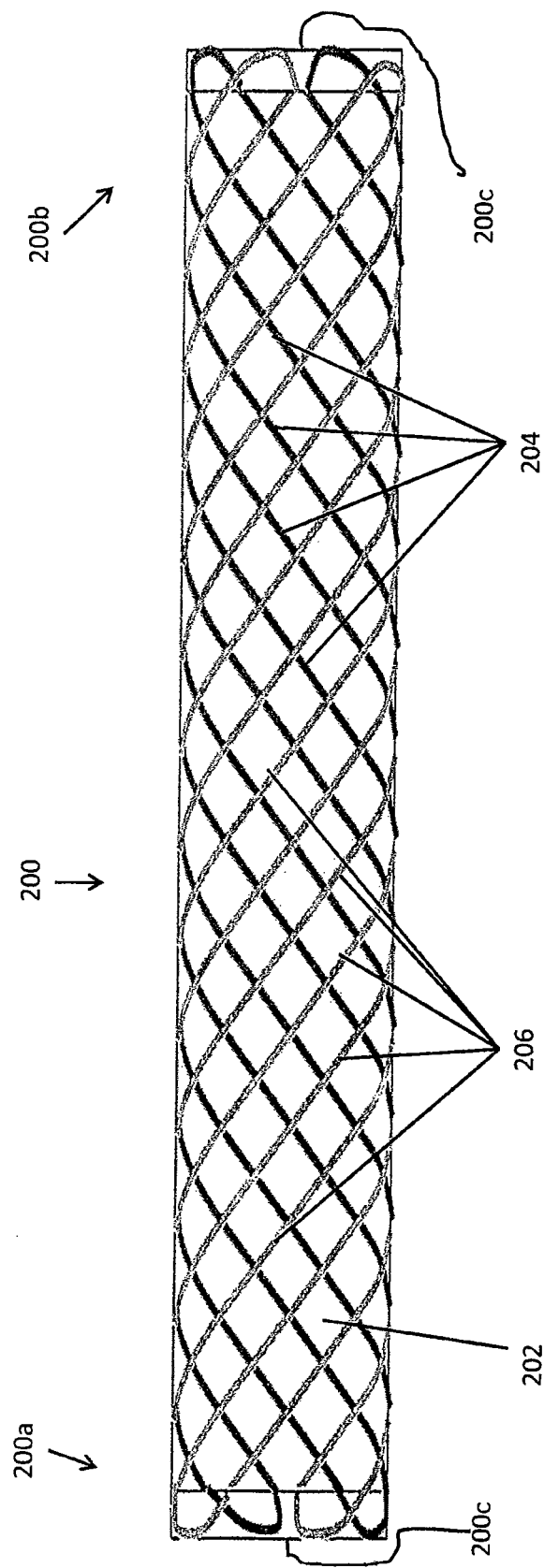
FIG. 2 illustrates a modified stent for use with an exemplary torsion constrainment introducer.

FIG. 2 illustrates modified tubular stent 200 for use with a torsion constrainment introducer, such as that described in U.S. Provisional Patent Appl. Ser. No. 61/407,635, entitled "Torsion Constrained Stent Delivery System," filed Oct. 28, 2010, and incorporated in its entirety herein by reference. Accordingly, stent 200 would not need a sheath for delivery which overcomes many of the problems associated with the use of a sheath for stent delivery. It is contemplated that stent can be introduced using various means, including but not limited to torsion constrained delivery systems and even a sheath should that be needed or desired.

Stent 200 has proximal portion 200a, distal portion 200b, and lumen 200c extending throughout. Stent 200 is preferably, although not required, a self-expanding, double helical stent that has the tendency to radially collapse when opposite rotational forces are applied to the ends of stent 200 and radially expand when the forces are released. Stent 200 comprises wire 204 and suture 206. By way of non-limiting example, stent 200 may be constructed as a non-woven mesh formed from a metal or polymer or a laser cut pattern formed in a metal stent. Stent 200 may also be formed from a bioabsorbable material. Indeed, it is also contemplated that stent 200 can have other configurations, such as a braided (platted) helical pattern. An example of a woven stent that may benefit from the discovery of the principles illustrated herein is the EVOLUTION® (Wilson-Cook Medical Inc.), but it is contemplated that other indwelling medical devices, such as stents, will also benefit from the principles illustrated.

Stent helical wire strand 204 is preferably made from, although not required, nitinol, although other materials are contemplated, including but not limited to, stainless steel and any medical-grade material having properties similar to nitinol such that the material is configurable into a biased position and when out from that position is biased to resume the initial biased position. Wire 204 is about 0.2 mm in diameter and is woven to have a pitch of about 55 mm, although other dimensions are contemplated depending upon the area to be treated and the needs of the patient. Wire 204 is wrapped over a stainless steel mandrel (other materials are contemplated) forming a right-handed helical pattern and heat-set to assume an expanded, uncompressed state. It is contemplated that the diameter and pitch of helical wire strand 204 can be altered to provide additional radial force to stent 200, for example by increasing the diameter of helical wire strand 204 and/or increasing the pitch.

Sutures 206 are applied over helical wire strand pattern 204 to form a left-handed, opposite, helical pattern. It is contemplated that suture 206 can be applied to the inside or outside of helical wire strand 204. It is also contemplated that the right and left-hand helical orientations may be reversed. Additionally, it is contemplated, although but not required, that sutures may be tied or knotted to wire strand 204, or portion(s) thereof, to provide additional rigidity, such as by knotting suture 206 at each point suture 206 crosses over (or under) helical wire strand 204.

Suture 206 is preferably made from ultra high molecular weight polyurethane although other medical grade materials are contemplated, including but not limited to, nylon and polymers. Suture 206 is about 0.3 mm in diameter, although other dimensions are contemplated depending upon the area to be treated and the needs of the patient.

Silicone membrane 202 is applied over helical wire strand 204 and suture 206 assembly thereby holding suture 206 into place and seal stent. Other types of coatings are contemplated, including but not limited to, flexible coatings, depending upon the needs of the patient and the area to be treated.

Stent 200 is about 15-25 mm in diameter and about 5-15 cm long in an expanded state, although other dimensions are contemplated depending upon the area to be treated and the needs of the patient. Although preferably sized for use in the esophageal region, other dimensions, uses, and locations are contemplated depending upon the needs of the patient and the area to be treated. Indeed, other configurations are contemplated depending upon the needs of the patient and the area to be treated.

Figure 3:
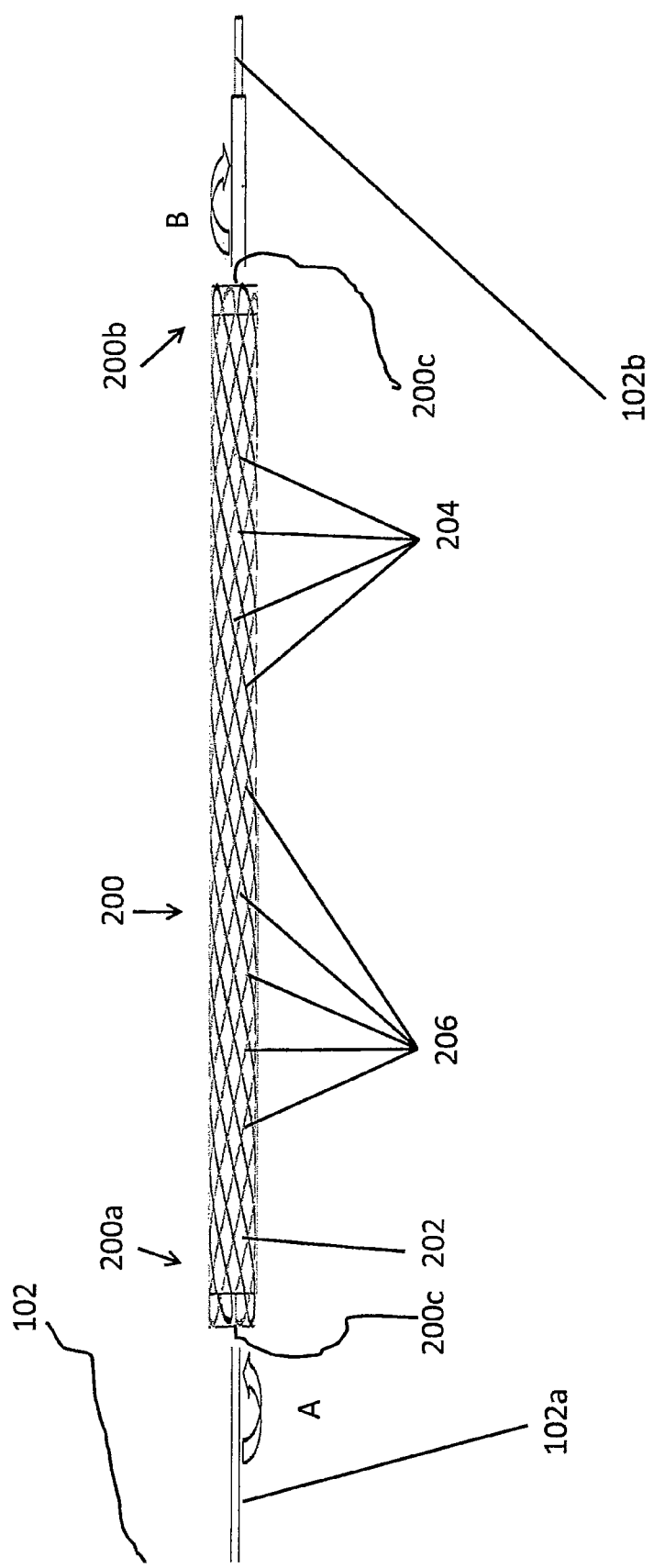
FIG. 3 illustrates a modified stent mounted on an exemplary torsion constrainment introducer in a compressed state.

FIG. 3 illustrates modified double helical stent 200 mounted onto exemplary torsion constrainment introducer 102 in a compressed state, such that proximal portion 200a of stent 200 is attached to proximal portion 102a of introducer 102, and distal portion 200b of stent 200 is attached to distal portion 102b of introducer 102. When proximal portion 200a and distal portion 200b of stent 200 are rotated in opposite directions, an illustrated by Arrows A and B, such as when using torsion introducer 102, or other means, stent 200 compresses, collapses evenly, without the formation of a ridge. Thus, when a torsion force is applied to stent 200, in a manner that decreases the pitch and the diameter of helical wire strand 204, stent 200 collapses. Suture 206 has an extremely low column strength such that it allows stent 200 membrane to create a fold in a manner that does not result in ridge 104, as illustrated in FIG. 1C. Stent 200 can then be directed to a treatment area and deployed.

Again referring to FIG. 3, because stent 200 has a double helical pattern, it continues to perform as well as current double helical stents, such as the EVOLUTION® (Wilson-Cook Medical Inc.). An additional benefit of stent 200 is that it foreshortens less than typical double helical stents, and it may be configured such that it does not foreshorten at all, or such that it foreshortens only to a negligible degree. Foreshortening is a property whereby a stent in an expanded state is longer than when it is in a compressed state. Foreshortening may result in a stent being deployed in the wrong position because the stent shortens during expansion, such as when expanding after being deployed. Accurate placement of the stent may be important in certain applications, for example to prevent stent migration or to properly open a stricture along the entire length of the stricture.

Figure 4:
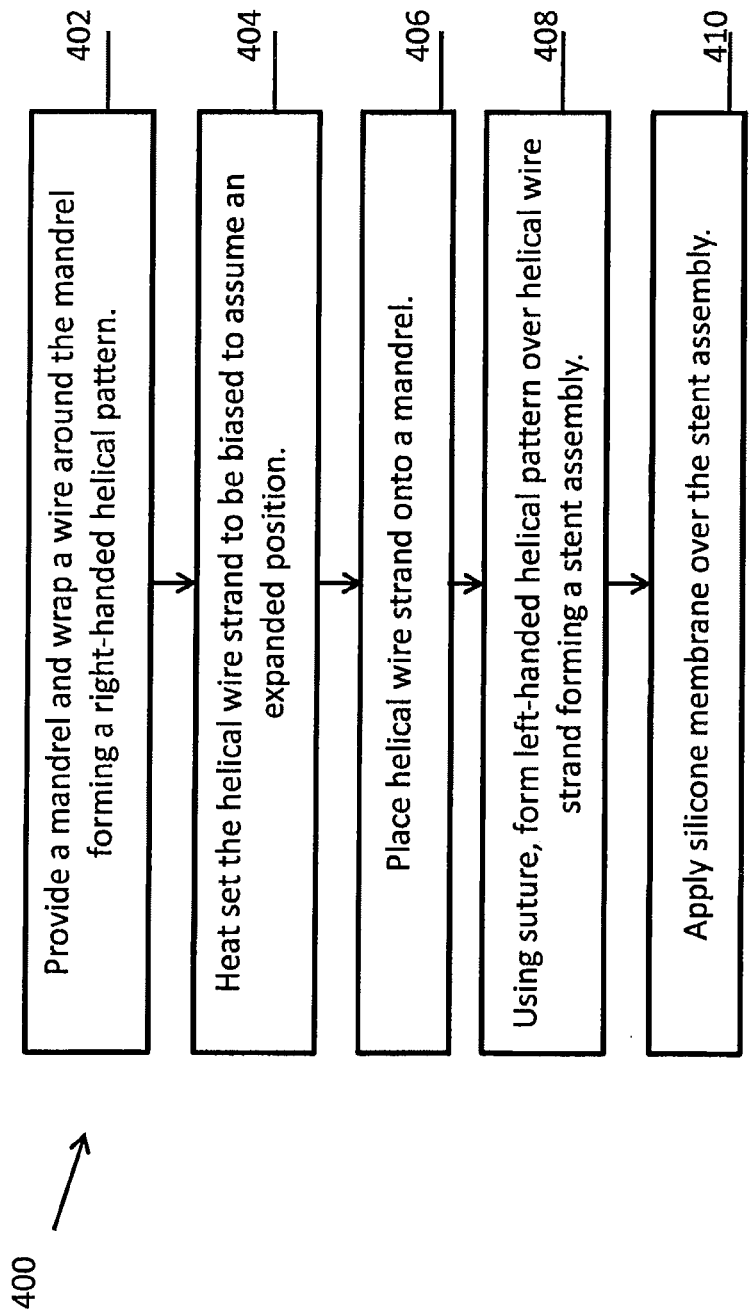
FIG. 4 illustrates a method for manufacturing a modified stent such as that illustrated in FIGS. 2-3.

FIG. 4 illustrates a method for manufacturing a modified stent that collapses and expands in a uniform, predictable manner 400, such as that illustrated in FIGS. 2-3. At block 402, a mandrel is provided, preferably made from stainless steel, although other materials are contemplated, and a wire is wrapped around the mandrel forming a right-handed helical pattern, such as that illustrated in FIGS. 2-3. Wire is preferably made from nitinol, although nitinol is not required; other materials are contemplated, including but not limited to, stainless steel and any medical-grade material having properties similar to nitinol such that the material is configurable into a biased position and when out from that position is biased to resume the initial biased position. Wire is about 0.2 mm in diameter, and is woven to have a pitch of about 55 mm, although other dimensions are contemplated depending upon the area to be treated and the needs of the patient. It is contemplated that the diameter and pitch of helical wire strand can be altered to provide additional radial force to stent, for example by increasing the diameter of helical wire strand and/or increasing the pitch.

At block 404, the helical wire strand is heat-set to be biased to assume an expanded position.

At block 406, the helical wire strand is placed onto a mandrel. The mandrel is preferably made from polytetrafluoroethylene, although other materials may be used.

At block 408, a left-handed, opposite helical pattern is formed using the suture over the previously formed helical wire strand, thereby forming a stent assembly. The suture is preferably made from ultra high molecular weight polyurethane although other medical grade materials are contemplated, including but not limited to, nylon and polymers. The suture is about 0.3 mm in diameter, although other dimensions are contemplated depending upon the area to be treated and the needs of the patient. It is contemplated that the suture can be applied to the inside or outside of helical wire strand by first forming a suture pattern, then forming a wire pattern over the suture, or visa versa. Additionally, it is contemplated, but not required, that the sutures may be tied or knotted to stent strand, or portion(s) thereof, to provide additional rigidity, such as by knotting suture at each point suture crosses over (or under) helical wire strand. It is also contemplated that the right and left-hand helical orientations may be reversed.

At block 410, an optional silicone membrane is applied over the stent assembly. Silicone membrane helps to hold the suture into place and seal the stent. Other types of coatings are contemplated, including but not limited to, flexible coatings, depending upon the needs of the patient and the area to be treated.

From the foregoing, it can be seen that the present disclosure illustrates apparatuses and methods for an improved indwelling medical device, such as a double helical or braided (platted) helical wire stent, that provides for uniform collapsing and expansion such that the stent collapses and expands in a uniform, predictable manner, reduces foreshortening, and provides a durable, stable, and reliable stent.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A stent comprising:
  a first elongated tubular helical pattern consisting of a unitary metallic wire configured into a plurality of adjacently disposed parallel first wire strands each having a right-handed first pitch, a proximal portion, a distal portion, a lumen extending between the proximal portion and the distal portion, and a first diameter of the first elongated tubular helical pattern, each of said adjacently disposed parallel first wire strands being disposed between a pair of other adjacently disposed parallel first wire strands, wherein the first elongated tubular helical pattern is configurable into a radially compressed state comprising a second diameter less than the first diameter when a rotational force is applied to the proximal portion of the first elongated tubular helical pattern and an opposite rotational force is applied to the distal portion of the first elongated tubular helical pattern; wherein when in the radially compressed state, the first elongated tubular helical pattern is biased to assume an uncompressed state; and
  a second elongated tubular helical pattern consisting of a unitary non-metallic suture configured into a plurality of adjacently disposed parallel second sutures each having a left-handed second pitch opposite the right-handed first pitch of the first elongated tubular helical pattern, each of said adjacently disposed parallel second sutures being disposed between a pair of other adjacently disposed parallel second sutures, wherein the second elongated tubular helical pattern comprises a proximal portion and a distal portion and;
  wherein the first elongated tubular helical pattern and the second elongated tubular helical pattern are in communication with each other to form a stent wall consisting of a double helical pattern and having a uniform configuration when in the compressed state.

2. The stent of claim 1, wherein the second elongated tubular helical pattern is configured over the first elongated tubular helical pattern.

3. The stent of claim 1, wherein the second sutures are knotted to at least a portion of the first wire strands.

4. The stent of claim 1, wherein the unitary metallic wire comprises a diameter of about 0.2 mm.

5. The stent of claim 1, wherein the unitary non-metallic suture comprises a diameter of about 0.3 mm.

6. The stent of claim 1, wherein the stent further comprises a coating covering at least a portion of the stent wall.

7. The stent of claim 6, wherein the coating comprises a silicone membrane.

8. The stent of claim 1, wherein the unitary metallic wire comprises nickel titanium (nitinol).

9. The stent of claim 1, wherein the unitary non-metallic suture comprises ultra high molecular weight polyurethane.

10. The stent of claim 1, wherein the first elongated tubular helical pattern comprises a pitch of about 55 degrees.

* * * * *